(12) United States Patent
Wang et al.

(10) Patent No.: US 10,130,757 B2
(45) Date of Patent: Nov. 20, 2018

(54) METHOD AND SYSTEM FOR LEAKAGE DETECTION IN PORTABLE MEDICAL DEVICES

(71) Applicant: MEDTRONIC MINIMED, INC., Northridge, CA (US)

(72) Inventors: Yongbo Wang, Arcadia, CA (US); Steve Chow, Northridge, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 609 days.

(21) Appl. No.: 14/701,902

(22) Filed: May 1, 2015

(65) Prior Publication Data

US 2016/0317739 A1 Nov. 3, 2016

(51) Int. Cl.
*A61M 5/142* (2006.01)
*A61M 5/168* (2006.01)
*A61M 5/50* (2006.01)

(52) U.S. Cl.
CPC .... *A61M 5/14244* (2013.01); *A61M 5/16831* (2013.01); *A61M 5/5086* (2013.01); *A61M 2205/15* (2013.01); *A61M 2205/18* (2013.01)

(58) Field of Classification Search
CPC .......... A61M 5/14244; A61M 5/16831; A61M 5/5086; A61M 2205/18; A61M 2205/50; A61M 2205/52; G01N 27/048
USPC .......................................................... 607/2
See application file for complete search history.

(56) References Cited

U.S. PATENT DOCUMENTS

| | | |
|---|---|---|
| 4,755,173 A | 7/1988 | Konopka et al. |
| 5,391,250 A | 2/1995 | Cheney, II et al. |
| 5,485,408 A | 1/1996 | Blomquist |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,544,212 B2 | 4/2003 | Galley et al. |
| 6,558,351 B1 | 5/2003 | Steil et al. |

(Continued)

*Primary Examiner* — Catherine Voorhees
*Assistant Examiner* — Roland Dinga
(74) *Attorney, Agent, or Firm* — Medtronic MiniMed, Inc.

(57) ABSTRACT

A medical therapy system including liquid detection is disclosed. A medical therapy includes a case with an interior and an exterior. Within the interior of the case is the liquid detection system that includes a first electrode set with a first positive electrode and a first negative electrode. The liquid detection system further includes an impedance measurement circuit coupled to the first electrode set to determine impedance values between the first positive electrode and the first negative electrode. A threshold detector compares impedance values between the first electrode set to a first threshold impedance. A microprocessor is programmed to initiate an alarm when measured impedance from the first electrode set is below the first threshold impedance.

17 Claims, 5 Drawing Sheets

(56) References Cited

U.S. PATENT DOCUMENTS

| | | |
|---|---|---|
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 2007/0123819 A1 | 5/2007 | Mernoe et al. |
| 2010/0160861 A1 | 6/2010 | Causey, III et al. |
| 2010/0160902 A1* | 6/2010 | Aeschilimann ........ A61B 5/053 604/891.1 |

* cited by examiner

METHOD AND SYSTEM FOR LEAKAGE DETECTION IN PORTABLE MEDICAL DEVICES

FIELD OF THE INVENTION

This invention relates to portable external infusion systems.

BACKGROUND OF THE INVENTION

Diabetes is a disease in which the body does not produce or properly use insulin. Approximately 13 million people in the United States have been diagnosed with some form of diabetes. Type 1 diabetes results from the body's failure to produce insulin. Type 2 diabetes results from insulin resistance in which the body fails to properly use insulin. To effectively manage the disease, diabetics must closely monitor and manage their blood glucose levels through exercise, diet and medication. In particular, both Type 1 and Type 2 diabetics rely on insulin delivery to control their diabetes. Traditionally, insulin has been injected with a syringe multiple times during the day, usually self-administered by the diabetic. In recent years, external infusion pump therapy has been increasing, especially for delivering insulin to diabetics using devices worn on a belt, in a pocket, or the like, with the insulin delivered from a reservoir via a catheter with a percutaneous needle or cannula placed in the subcutaneous tissue.

External infusion devices allow Type 1 and Type 2 diabetics to better manage and control their diabetes. The external infusion device is intended to be used continuously and delivers insulin twenty-four hours a day according to a programmed plan unique to each pump wearer. A small amount of insulin, or a basal rate, is given continually. This insulin keeps the user's blood glucose levels in the desired range between meals and overnight. When food is eaten, the user programs the external infusion device to deliver a bolus of insulin matched to the amount of food that will be consumed. The user determines how much insulin will be given based on factors including insulin sensitivity, insulin duration, insulin-on-board, and the like. In many instances, external infusion devices include a processor that assists the user in making therapy decisions based on information provided by the user including blood glucose levels, carbohydrate intake, and/or information from the external infusion device. Exemplary devices are described in U.S. Pat. No. 6,554,798 issued on Apr. 29, 2003 to Mann et al., and entitled "External Infusion Device with Remote Programming, Bolus Estimator and/or Vibration Alarm Capabilities," which is specifically incorporated by reference herein.

Users of external infusion device therapy rely on the precision and control of the therapy. It is important to minimize unexpected compromises of the infusion device, such as unnoticed cracks that allow liquids to leak into the device. Such leaks could lead to unpredictable device behavior or even failure of the device. Thus, having reliable and robust leak detection is highly desirable so users can engage in activities such as bathing, showering or even walking in the rain without compromising their confidence in the reliability of their external infusion device.

SUMMARY OF THE DISCLOSURE

In one embodiment a medical therapy system including liquid detection is disclosed. A medical therapy includes a case with an interior and an exterior. Within the interior of the case is the liquid detection system that includes a first electrode set with a first positive electrode and a first negative electrode. The liquid detection system further includes an impedance measurement circuit coupled to the first electrode set to determine impedance values between the first positive electrode and the first negative electrode. A threshold detector compares impedance values between the first electrode set to a first threshold impedance. A microprocessor is programmed to initiate an alarm when measured impedance from the first electrode set is below the first threshold impedance.

In another embodiment a method of detecting fluid is disclosed. The method includes an operation that sets a first threshold impedance. In another operation impedance between a first set of electrodes is measured. Another operation stores the measured impedance to a memory while still another operation compares the measured impedance to the first threshold impedance. The method activates an alarm if the measured impedance is below the threshold impedance.

Other features and advantages of the invention will become apparent from the following detailed description, taken in conjunction with the accompanying drawings which illustrate, by way of example, various features of embodiments of the invention.

BRIEF DESCRIPTION OF THE DRAWINGS

A detailed description of embodiments of the invention will be made with reference to the accompanying drawings, wherein like numerals designate corresponding parts in the several figures.

DETAILED DESCRIPTION

As shown in the drawings for purposes of illustration, the invention is embodied as an element or component within a portable infusion system. While many embodiments describe measuring impedance between electrodes to determine the presence of liquid, the extent of the disclosure should not be construed to exclude measuring capacitance, inductance or resistance to accomplish the same objective. Rather, impedance along with capacitance, inductance, and resistance should all be considered interchangeable to those skilled in the art as being able to determine whether liquid is present on electrodes.

Figure 1A:
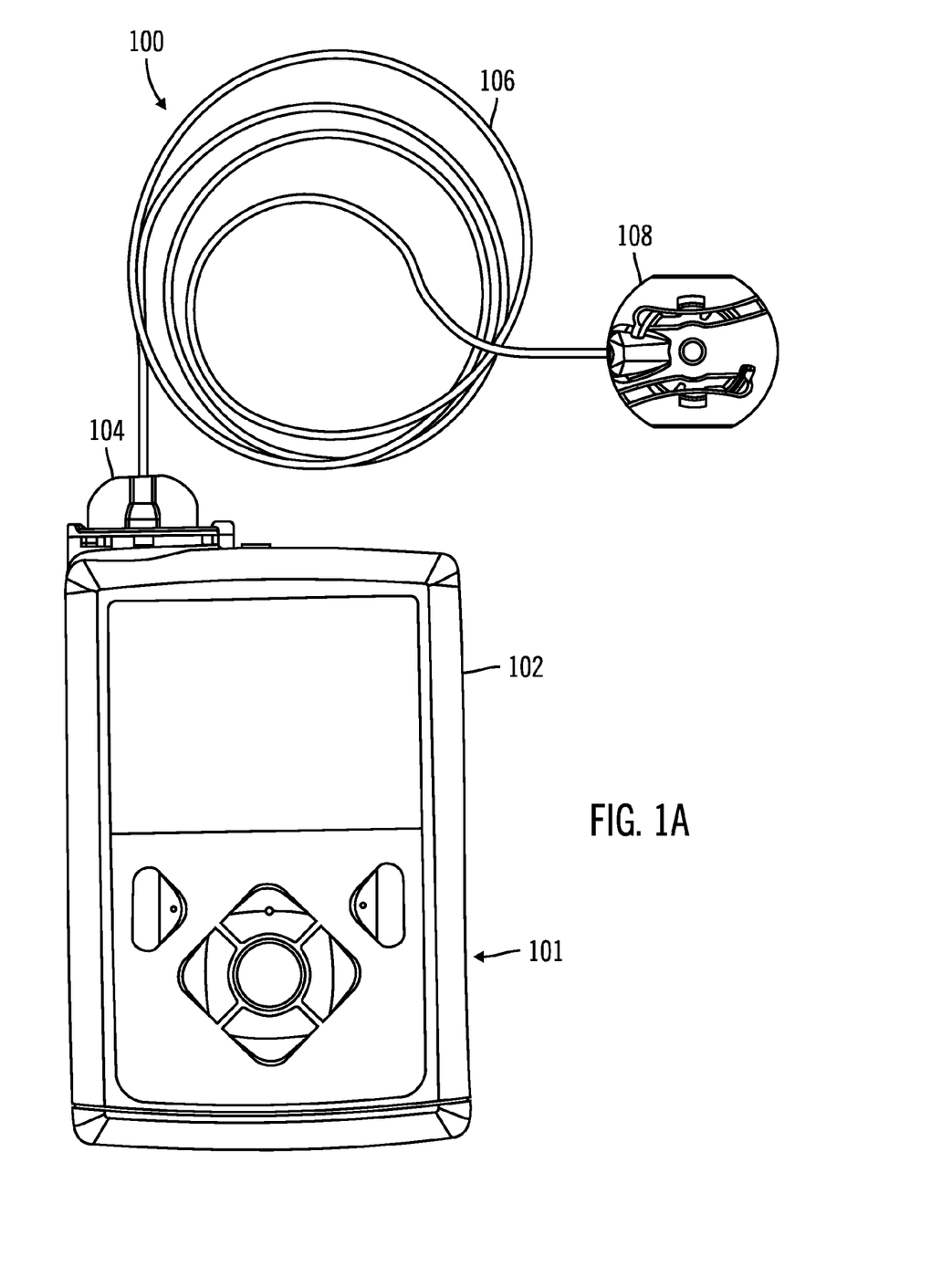
FIG. 1A is an exemplary illustration of elements within an infusion system, in accordance with embodiments of the present invention.

FIG. 1A is an exemplary illustration of elements within an infusion system 100, in accordance with embodiments of the present invention. The infusion system 100 includes an infusion pump 101 having a case 102 that contains a reservoir 104. The infusion pump 101 includes a mechanism that moves fluid from the reservoir 104 to an infusion set 108 via tubing 106. In some embodiments the infusion set 108 includes a cannula (not shown) that is coupled to the tubing 106 to deliver fluid from the infusion pump 101 into subcutaneous tissue of a user. When used for diabetes therapy, the reservoir 104 can be filled with insulin to be delivered via the infusion set 108.

In some embodiments the case 102 is made from polycarbonate, acrylonitrile butadiene styrene (ABS), or copolyester materials such as Eastman TRITAN to increase durability and to minimize the likelihood of liquid ingress such as water. In one embodiment, during the manufacturing process the case 102 is ultrasonically welded to completely seal major openings in the case. However, the case 102 does include other openings such as those for the reservoir 104 and battery, which are protected against liquid ingress by flexible o-rings with interference fits to their mating components. Furthermore, the reservoir 104 is designed to minimize the likelihood of fluid from the reservoir 104 leaking into the case 102. However, regardless of how robust and durable the case 102 and reservoir 104 are designed, real world usage can include repeated drops, crushes and pressure fluctuations that can eventually compromise the integrity of the case 102.

Figure 1B:
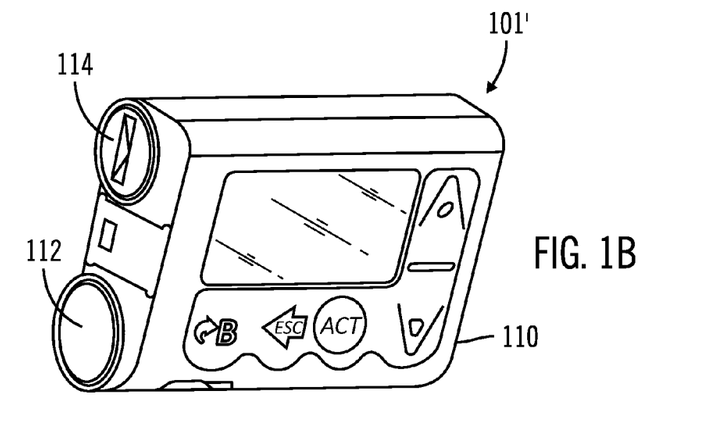
FIG. 1B is an additional embodiment of an infusion pump that can be used within the infusion system, in accordance with embodiments of the present invention.

FIG. 1B is an additional embodiment of an infusion pump 101' that can be used within the infusion system 100, in accordance with embodiments of the present invention. Infusion pump 101' includes a case 110 that is similar to the case 102. Similar design features and manufacturing techniques can be applied to both cases 102 and 110. For example, case 110 includes an opening 112 for a reservoir (not shown). Case 110 further includes an opening that is sealed by battery cap 114. Within the case 110 are electronics and mechanism that control the flow of fluid from the reservoir to the infusion set.

Figure 1C:
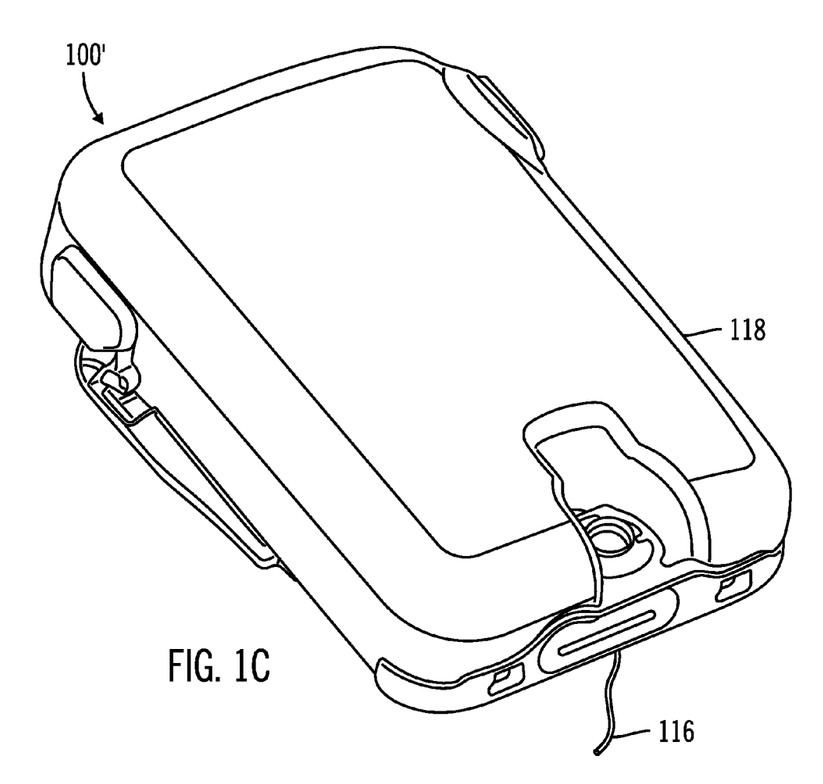
FIG. 1C is still a further embodiment of an infusion system, in accordance with embodiments of the present invention.

FIG. 1C is still a further embodiment of an infusion system 100', in accordance with embodiments of the present invention. The infusion system 100' shown in FIG. 1C is commonly referred to as a "patch pump". As illustrated, infusion system 100' lacks the tubing and infusion set found in infusion system 100 in FIG. 1A. Rather, in some embodiments, the infusion system 100' includes a cannula 116 that can be inserted to various depths within the user. A reservoir is contained within a case 118 of the infusion system 100'. The case 114 further contains electronics and mechanism that control dispensing of fluid within the reservoir through the cannula 116.

In embodiments where the infusion system 100, 100', or infusion pump 101' is used for diabetes therapy the user relies on precision control provided by the electronics within the infusion pump 101. Accordingly, integrity of the respective cases is important to protect sensitive electronics within the case from exposure to liquid. Liquid within the case can compromise the entire infusion system leading to malfunctions, unpredictable behavior or even complete failure of the infusion pump. As users rely on the infusion system to regulate blood sugar, detection and notification of the user regarding liquid in the pump case results in users having an opportunity to contact customer service to troubleshoot potential issues with the infusion system before catastrophic failure occurs.

Figure 2:
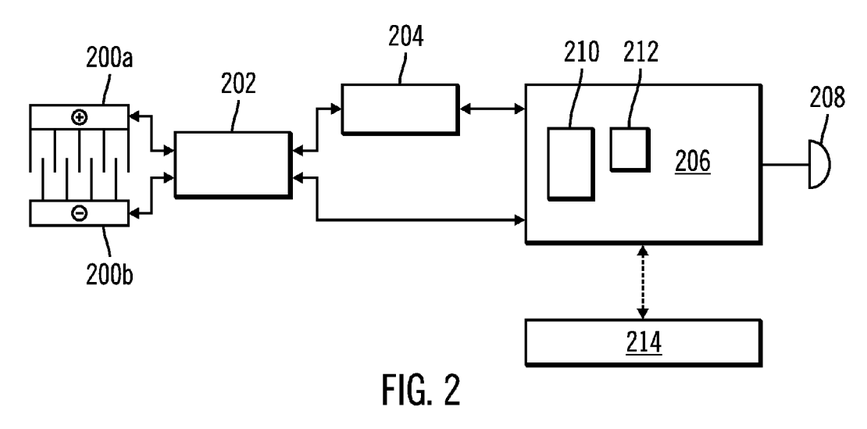
FIG. 2 is an exemplary block diagram of a liquid detection system for use in portable electronic devices, in accordance with embodiments of the present invention.

FIG. 2 is an exemplary block diagram of a liquid detection system for use in portable electronic devices, in accordance with embodiments of the present invention. The liquid detection system includes electrodes 200a and 200b that are connected to impedance circuitry 202. The impedance circuitry 202 is coupled to a threshold detector 204 which in turn is coupled to a microprocessor 206 having a memory 210. In some embodiments the impedance circuitry 202 is further optionally directly coupled to the microprocessor 206. In all embodiments, the microprocessor 206 is used to control an alarm 208. In one embodiment the microprocessor 206 is dedicated to the liquid detection system. In other embodiments the microprocessor 206 also performs additional processing for the infusion system.

In one embodiment electrodes 200a and 200b are comb shaped electrodes that include teeth that are offset as shown in FIG. 2. For purposes of illustration only, electrode 200a is shown as a positive electrode while electrode 200b is the negative electrode. When dry, the electrical impedance between electrodes 200a and 200b is greater than 100 mega Ohm. If liquid is introduced across the offset combs the impedance between the electrodes 200a and 200b is significantly reduced. The impedance circuitry 202 periodically converts the impedance into a measureable form, such as voltage or a digital value. The value from the impedance circuitry 202 is analyzed by the threshold detector 204 that sends a wake-up signal to the microprocessor 206 when a threshold impedance is measured across the electrodes 200a and 200b. Alternatively, periodic impedance values from the impedance measurement circuitry 202 can be recorded into the memory 210 of the microprocessor 206. The microprocessor 206 can further include software, hardware, or combinations thereof to analyze impedance values stored within the memory 210 for patterns to determine if there is liquid on the electrodes or if the circuit is simply in a high humidity environment. The illustration of the electrodes 200a and 200b as offset combs should not be construed as limiting. In other embodiments different electrode configurations can be used so long as liquid across the electrodes 200a and 200b creates a detectable change in impedance.

In some embodiments the threshold detector 204 is set low enough that impedance values caused by a worst case humidity condition does not trigger the wakeup to the microprocessor 206. For example, based on the operating parameters of the infusion system, the infusion pump can be placed in a maximum humidity environment with liquid detection circuits throughout the interior of the case. The minimum impedance values for the liquid detection circuits can be measured when the pump is operated within the maximum humidity environment thereby establishing a threshold value.

In other embodiments, the threshold detector 204 is set so a relatively high impedance value triggers the wakeup function of the microprocessor 206. In these embodiments, the wakeup function additionally activates the optional logging and analysis of impedance values to determine if fluctuations in ambient humidity caused the initial threshold detection. This embodiment can be beneficial for portable electronic systems because it can reduce power draw from the liquid detection circuit. Thus, when a relatively high threshold impedance value is registered, the liquid detection circuit begins recording impedance values in order to create an impedance history that can be analyzed for patterns caused by fluctuations in ambient humidity.

In still further embodiments, impedance values can be correlated to time using a clock 212 in order to create a dynamic threshold based on previous temporal impedance measurements. For example, the liquid detection circuit measures and records impedance values that decrease between 8 AM and 2 PM corresponding to increasing ambient humidity. Accordingly, the following day, the threshold values can be dynamically changed to reflect the ambient humidity of the previous day. Thus, as the humidity increases and decreases throughout the day, the threshold impedance value can dynamically change based on previously recorded data to avoid false alarms. Another technique that can be used to compensate for humidity and avoid false alarms of liquid on the electrodes is to monitor the rate of change of impedance.

Other embodiments include optional communication module 214 coupled with the microprocessor 206. The communication module 214 can include, but is not limited to wireless communication protocols such as Wi-Fi, BLUETOOH, BLUETOOTH LOW ENERGY, ZIGBEE, Z-WAVE, LTE and NFC. The communication module 214 enables access to location information along with corresponding weather data and weather forecasts that can be utilized to dynamically change the threshold impedance value of the liquid detection system.

In some embodiments, when the liquid detection system shown in FIG. 2 is applied to the infusion systems in FIGS. 1A-1C there may be additional sets of electrodes 200a and 200b placed at various locations within various compartments within the respective cases. Furthermore, both the threshold detector and the microprocessor can be programmed with different threshold impedances based on the location of electrodes. In one example, liquid detection electrodes can be located near the reservoir for infusion pump 101 and 101'. Upon being filled and installed within the infusion pump 101 the reservoir itself may contain insulin that was recently removed from a refrigerated space. Accordingly, as the insulin within the reservoir warms to ambient temperature condensation may form on the outside of the reservoir. As this is a known issue, the reservoir chamber is properly sealed and vented to allow potential condensate to naturally evaporate. To avoid false detection of fluid within the infusion pump the threshold impedance for the electrodes within the reservoir chamber may be very low. However, to ensure that any fluid within the reservoir chamber does not migrate to an originally sealed compartment, the threshold impedance values for another set of liquid detection electrodes may have a very high impedance threshold. In another embodiment, collection of impedance values from liquid detection electrodes within the reservoir chamber is paused for a period of time after a reservoir is installed. Similar features can also be used within and adjacent to the battery compartment to avoid false liquid detection upon replacement of the battery.

Figure 3:
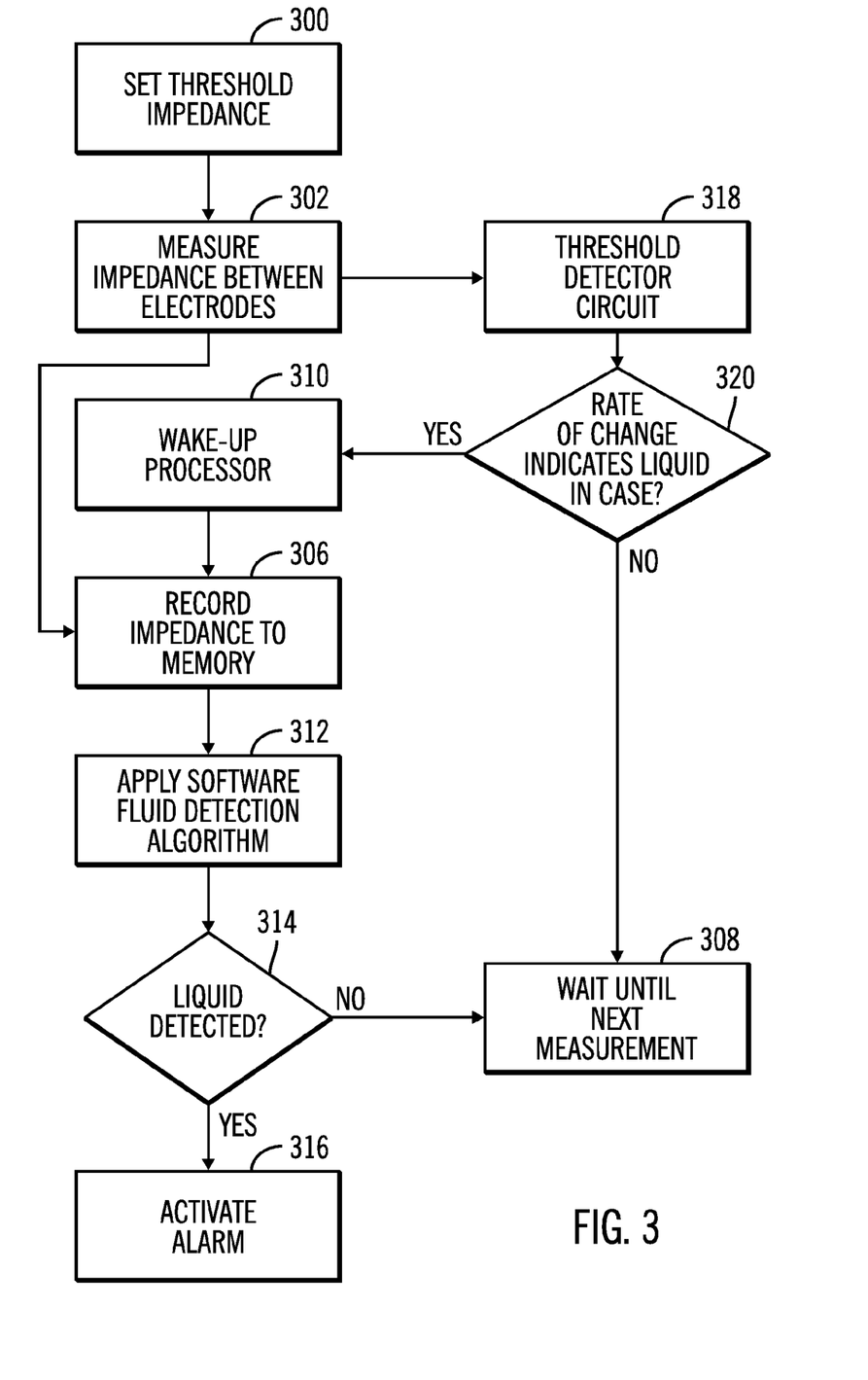
FIG. 3 is a flow chart illustrating exemplary operation of the liquid detection system, in accordance with embodiments of the present invention.

FIG. 3 is a flow chart illustrating exemplary operation of the liquid detection system, in accordance with embodiments of the present invention. The flow chart beings with operation 300 that sets an impedance threshold. As previously discussed, in various embodiments multiple threshold impedance values can be set for multiple liquid detection electrodes. Likewise, the threshold impedance can also by dynamically set based on previously measured values or weather forecasts. Operation 302 measures impedance between the liquid detection electrodes and can be initiated by a variety of triggers such as software or hardware timers. In still other embodiments where power consumption is not an issue or for extremely critical components impedance measurement can be taken continuously. In various embodiments the interval between impedance measurements is between one minute and 30 minutes. In some embodiments the interval between impedance measurements varies based on the time of day. For example, during regular sleeping hours the liquid detection system may only take an impedance measurement every 15 or 30 minutes. Conversely, during regular waking hours impedance measurements can be taken more frequently such as, but not limited to every minute or every five minutes. To accommodate various work schedules, in other embodiments a user is allowed to specify sleep and wake hours.

In some embodiments if operation 302 is initiated via software, operation 308 records the measured impedance to memory. In embodiments where operation 302 is initiated by hardware, the measured impedance is passed to a threshold detector circuit 318 that executes operation 320 to determine if the rate of change of impedance is indicative of liquid in the case. If operation 320 indicates liquid is in the case operation 310 wakes up the processor and operation 306 records the measured impedance to memory. In many embodiments regardless of whether the trigger of operation 302 is hardware, software or combinations of both, a time associated with the impedance measurement is also recorded into memory.

Operation 312 applies a fluid detection algorithm to the impedance values stored in memory resulting in operation 314 that determines if liquid is detected. If operation 314 detects liquid operation 316 activates an alarm. The alarm that is activated can be audible, tactile (vibration), visual or a combination thereof. If operation 314 does not detect liquid, operation 308 waits until the next impedance measurement is taken via operation 302.

Figure 4A:
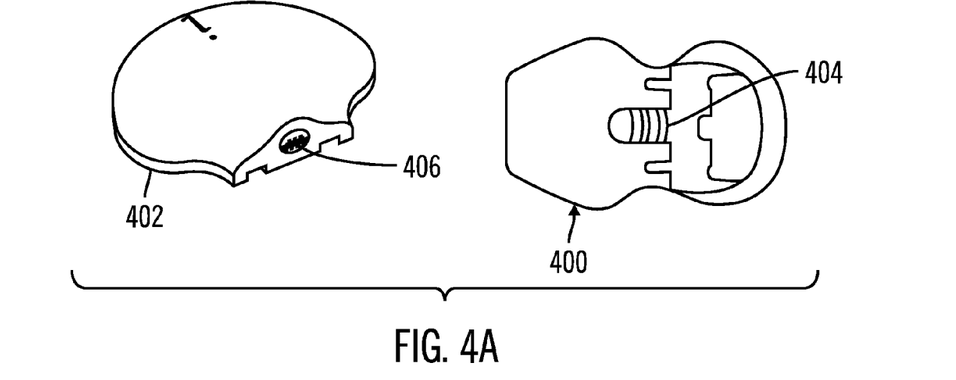
FIGS. 4A and 4B are exemplary illustrations of a sensor set and transmitter that can be used in conjunction with the infusion system, in accordance with embodiments of the present invention.
Figure 4B:
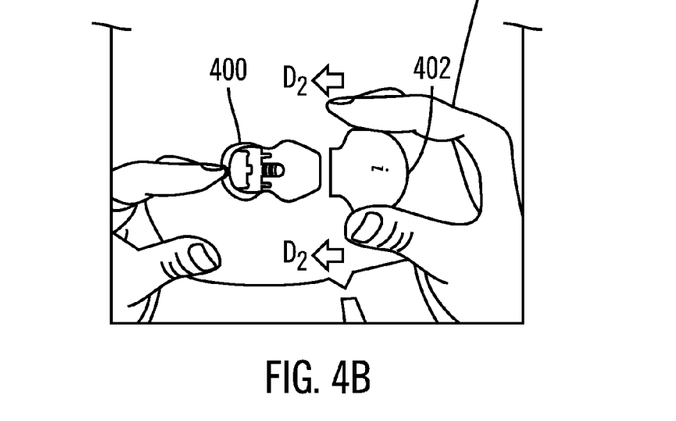

FIGS. 4A and 4B are exemplary illustration of a sensor set 400 and transmitter 402 that can be used in conjunction with the infusion system, in accordance with embodiments of the present invention. The sensor set 400 includes a sensor (not shown) that in some embodiments is inserted into subcutaneous tissue of a user. The sensor set 400 further includes a connector 404 that is coupled to the sensor. The sensor includes multiple electrodes that are coupled to corresponding contacts on the connector 404. The transmitter 402 includes a port 406 that receives to connector 404. Within the port 406 are pins that mate with the connector 404 contacts. The pins within the transmitter are coupled to a circuit board that includes a power supply and electronic circuitry that enables operation of the sensor set 400 and wireless transmission of data from the sensor 400 to the infusion system. FIG. 4B shows coupling of the transmitter 402 to the sensor set 400 after the sensor set 400 has been inserted into the user. Coupling of the transmitter is accomplished by supporting the sensor set 400 while moving the transmitter 402 in direction D1 while aligning the port and connector.

In many embodiments a power supply within the transmitter 402 allows the transmitter to be reused with multiple sensors before being disposed of or alternatively being recharged. However, when the sensor is inserted into the user it is possible, however unlikely, for bodily fluid such as blood to be released from the insertion site. Thus, due to the possible introduction of fluid near the port 406 it would be beneficial to include a fluid detection system within the transmitter 402. Accordingly, the fluid detection system described above should not be construed to be used exclusively with infusion systems, subcutaneous sensors, or even electronic devices having cases. Instead, the fluid detection system described above could be used in any application requiring the detection of liquid. Examples include, but are not limited to detection of undesirable liquid leakage proximate to intravenous injection sites or catheter sites. In still other embodiments, the liquid detection system could be adapted to measure humidity based on impedance between the electrodes.

While the description above refers to particular embodiments of the present invention, it will be understood that many modifications may be made without departing from the spirit thereof. The accompanying claims are intended to cover such modifications as would fall within the true scope and spirit of the present invention. The presently disclosed embodiments are therefore to be considered in all respects as illustrative and not restrictive. The scope of the invention being indicated by the appended claims, rather than the foregoing description, and all changes which come within the meaning and range of equivalency of the claims are therefore intended to be embraced therein.

What is claimed is:

1. A medical therapy system comprising:
   a case having an interior and an exterior; and
   a liquid detection system located within the interior of the case, the liquid detection system including
      a first electrode set, the first electrode set including a first positive electrode and a first negative electrode,
      an impedance measurement circuit coupled to the first electrode set to determine impedance values between the first positive electrode and the first negative electrode,
      a threshold detector to compare the impedance values of the first electrode set to a first threshold impedance, and
      a microprocessor programmed to initiate an alarm when impedance measured by the impedance measurement circuit of the first electrode set is below the first threshold impedance, wherein the microprocessor further includes a memory and a clock, the microprocessor further programmed to store the impedance values from the first electrode set in the memory with a corresponding time from the clock.

2. The medical therapy system as defined in claim 1, wherein the liquid detection system includes a second electrode set located in a different location within the case than the first electrode set, the second electrode set further coupled to the impedance measurement circuit such that the threshold detector and microprocessor distinguish between signals from the first electrode set and the second electrode set.

3. The medical system as defined in claim 2, wherein the threshold detector includes a second threshold impedance being different than the first threshold impedance.

4. The medical system as defined in claim 3, wherein the microprocessor is further programmed to store impedance values from the second electrode set in the memory.

5. The medical system as defined in claim 4, wherein the microprocessor is further programmed to store the impedance values from the second electrode set in the memory with a corresponding time from the clock.

6. The medical system as defined in claim 5, wherein the first threshold impedance and the second threshold impedance are dynamically set throughout the day based on stored impedance values and corresponding times.

7. The medical system as defined in claim 4, wherein the first threshold impedance and the second threshold impedance are set based on stored impedance values.

8. The medical therapy system as defined in claim 1, wherein the first threshold impedance is set based on stored impedance values.

9. The medical system as defined in claim 1, wherein the first threshold impedance is dynamically set throughout a day based on stored impedance values and corresponding times.

10. The medical system as defined in claim 9, wherein prior to initiating the alarm the microprocessor determines a rate of change of impedance based on the impedance values of the first electrode set and the stored impedance values, the rate of change of impedance being compared to a threshold rate of change impedance and initiation of the alarm occurs if the rate of change of impedance is greater than the threshold rate of change impedance.

11. In a case having an interior and an exterior, a method of detecting fluid within the interior of the case, comprising:
    setting a first threshold impedance;
    measuring impedance between a first set of electrodes, the first set of electrodes including a first positive electrode and a first negative electrode;
    storing the measured impedance to a memory with a corresponding time from a clock;
    comparing the measured impedance to the first threshold impedance; and
    if the measured impedance is below the first threshold impedance, activating an alarm.

12. The method of detecting fluid as defined in claim 11, wherein before activating the alarm, the method further comprises:
    determining a rate of change of impedance based on the measured impedance and a previous impedance value stored in the memory; and
    comparing the rate of change of impedance with a threshold rate of change, the alarm being activated if the rate of change of impedance is above the threshold rate of change.

13. The method of detecting fluid as defined in claim 12, wherein setting the first threshold impedance is based on stored measured impedance.

14. The method of detecting fluid as described in claim 12, wherein a second set of electrodes measures impedance in a different location than the first set of electrodes.

15. The method of detecting fluid as described in claim 14, wherein the measured impedance from the second set of electrodes is stored in the memory with a corresponding time from the clock.

16. The method of detecting fluid as described in claim 14, wherein a second threshold impedance is set, the second threshold impedance being different from the first threshold impedance, the second threshold impedance being further compared to the impedance measured by the second set of electrodes.

17. The method of detecting fluid as described in claim 11, wherein the first threshold impedance is dynamically set throughout a day based on stored measured impedance and corresponding time.

* * * * *